United States Patent
de Rijk

(10) Patent No.: US 8,916,050 B2
(45) Date of Patent: Dec. 23, 2014

(54) METHODS AND COMPOSITIONS FOR TREATMENT OF WATER

(75) Inventor: Jan de Rijk, Veenendaal (NL)

(73) Assignee: Special Water Patents B.V., Veneendaal (NL)

( * ) Notice: Subject to any disclaimer, the term of this patent is extended or adjusted under 35 U.S.C. 154(b) by 1247 days.

(21) Appl. No.: 10/596,095

(22) PCT Filed: Sep. 27, 2005

(86) PCT No.: PCT/IB2005/003665
§ 371 (c)(1),
(2), (4) Date: Jun. 4, 2007

(87) PCT Pub. No.: WO2006/035320
PCT Pub. Date: Apr. 6, 2006

(65) Prior Publication Data
US 2008/0035580 A1    Feb. 14, 2008

Related U.S. Application Data

(60) Provisional application No. 60/612,919, filed on Sep. 27, 2004.

(51) Int. Cl.
*C02F 1/50* (2006.01)
(Continued)

(52) U.S. Cl.
CPC . *C02F 1/50* (2013.01); *A01N 59/06* (2013.01); *A01N 37/36* (2013.01); *A01N 59/00* (2013.01); *C02F 1/32* (2013.01); *C02F 1/78* (2013.01); *C02F 9/00* (2013.01); *C02F 2103/42* (2013.01)
USPC .. 210/748.11; 210/760; 210/764; 252/182.35

(58) Field of Classification Search
CPC .............. C02F 1/32; C02F 1/50; C02F 1/78; C02F 1/001; C02F 1/02; C02F 1/72; C02F 9/00; C02F 2103/42; A01N 37/36; A01N 59/00; A01N 59/02; A01N 59/04; A01N 59/06; A01N 59/08; A01N 2300/00
USPC ................ 210/764, 748.1–748.15, 749, 760; 252/175, 178, 186.1, 188.1, 363.5, 252/182.11, 182.35, 189, 192; 424/682, 424/715, 717, 722; 510/199, 488, 514, 531; 5/748.1–748.15, 749, 760
See application file for complete search history.

(56) References Cited

U.S. PATENT DOCUMENTS 4,618,914 A    10/1986 Sato et al.
4,725,455 A    2/1988  Taha
(Continued)

FOREIGN PATENT DOCUMENTS

DE    4330597         3/1995
EP    0494373 A1      7/1992
JP    2000063894 A  * 2/2000

OTHER PUBLICATIONS

Machine translation of JP 2000-063894 (obtained from JPO Aug. 2010).*

(Continued)

*Primary Examiner* — Lucas Stelling
(74) *Attorney, Agent, or Firm* — Frost Brown Todd LLC

(57) ABSTRACT

The present invention relates to compositions and their use for the treatment of water. In one embodiment, the invention provides for a compositions and their use for the treatment of microorganisms. This invention also provides compositions and their use to provide clean water in an environmentally-friendly manner. In another embodiment, the invention provides for compositions and their use in combination with common equipment for controlling the growth of micro-organisms, such as with an ozonator or UV-C lamp, in a water system such as in hot tub or pool. Additionally, the specification describes methods and compositions for controlling the growth of microorganisms in an aqueous system. Using the methods and compositions, one treats an aqueous system with an amount effective to control the growth of at least one microorganism. Accordingly, several advantages of the invention are providing improved water treatment, providing environmentally-friendly treatment, providing a more user-friendly treatment, and providing water that is better for human health.

35 Claims, 2 Drawing Sheets

(51) Int. Cl.
- *A01N 59/06* (2006.01)
- *A01N 37/36* (2006.01)
- *A01N 59/00* (2006.01)
- *C02F 1/32* (2006.01)
- *C02F 1/78* (2006.01)
- *C02F 9/00* (2006.01)
- *C02F 103/42* (2006.01)

(56) References Cited

U.S. PATENT DOCUMENTS

| | | | |
|---|---|---|---|
| 4,747,978 A * | 5/1988 | Loehr et al. | 252/175 |
| 4,830,773 A | 5/1989 | Olson | |
| 5,281,351 A | 1/1994 | Romeo et al. | |
| 5,443,751 A | 8/1995 | Mazzola | |
| 5,599,781 A | 2/1997 | Haeggberg et al. | |
| 5,663,132 A | 9/1997 | Talley | |
| 5,707,534 A * | 1/1998 | Del Corral et al. | 210/755 |
| 5,741,768 A | 4/1998 | Falbaum et al. | |
| 5,789,361 A | 8/1998 | Talley | |
| 5,863,345 A | 1/1999 | Talley | |
| 6,258,772 B1 | 7/2001 | Yeggy et al. | |
| 6,825,159 B2 | 11/2004 | Man et al. | |
| 2002/0016278 A1 * | 2/2002 | Barbeau et al. | 510/480 |
| 2002/0037260 A1 | 3/2002 | Budny et al. | |
| 2005/0003979 A1 | 1/2005 | Lentsch | |

OTHER PUBLICATIONS

"The Green Chelate: A green alternative to EDTA, NTA, Phosphonate and Phosphates" akzonNobel.com.*

Dictionary definition of "glyconic acid," dictionary.com.*

Daisan, K. et al., Patent Abstracts of Japan, vol. 2000(5) (Sep. 14, 2000).

International Search Report dated Mar. 27, 2006 for Application No. PCT/IB2005/003665.

Written Opinion dated Mar. 27, 2007 for Application No. PCT/IB2005/003665.

Office Action dated Nov. 17, 2011 for U.S. Appl. No. 11/912,839.

Office Action dated Jul. 3, 2014 for U.S. Appl. No. 11/912,839.

Siegenthaler, Dr. Danny, "Importance of Skin's pH.," 2004, downloaded from www.naturalhealthweb.com Jun. 19, 2014.

* cited by examiner

METHODS AND COMPOSITIONS FOR TREATMENT OF WATER

CROSS REFERENCE TO RELATED APPLICATIONS

This application claims priority under 35 U.S.C. 119 to U.S. provisional application Ser. No. 60/612,919, filed Sep. 27, 2004, and entitled "METHOD AND COMPOSITION OF MATTER FOR TREATMENT OF WATER" the disclosure of which is hereby expressly incorporated herein by reference.

FIELD OF THE INVENTION

The present invention relates to compositions and their use for the treatment of water. In one embodiment, the invention provides for a compositions and their use for the treatment of micro-organisms. This invention also provides compositions and their use to provide clean water in an environmentally-friendly manner. In another embodiment, the invention provides for compositions and their use in combination with common equipment for controlling the growth of micro-organisms, such as with an ozonator or UV-C lamp, in a water system such as in hot tub or pool. Additionally, the specification describes methods and compositions for controlling the growth of microorganisms in an aqueous system. Using the methods and compositions, one treats an aqueous system with an amount effective to control the growth of at least one microorganism. Accordingly, several advantages of the invention are providing improved water treatment, providing environmentally-friendly treatment, providing a more user-friendly treatment, and providing water that is better for human health.

BACKGROUND OF THE INVENTION

During the past few decades, water has become increasingly important to our modern lifestyles, especially, for relaxation and social gatherings in pools and hot tubs. More and more people build their own swimming pools inside of their homes or in their gardens and stay healthy by training their bodies in water regularly. Although water is available in many places across our planet, a reliable supply of clean water is less easy to obtain.

During the last decade, the hot tub was presented on the market as a healthy and relaxing bath, to reduce stress and relax in warm water of ca. 100° F. In these easy-to-install hot tubs, jets are installed to pump the water under high pressure within the bath, where the water power relaxes the muscles. Also, a hot tub bath has been shown to be healthy and decrease blood pressure. Taking a bath in a hot tub also became a social affair—a place where everyone can enjoy the warm water and relax after a hard day's work. This is the same with swimming pools, although swimming pools are used more for sport and conditioning. However, for a pool outside, good weather is required as well as a lot of space.

Especially in pools and hot tubs, where the water temperature is relatively high, are risky environments for rapid bacterial growth. That is why treatment of hot tub water is needed. Presently, vast quantities of chlorine are used in combination with specific bacteria-killing equipment, like ozonators or UV-C lighting. This is due to the fact that chlorine kills and removes sessile bacterial slime layers from the walls, whereas ozone or UV-C kills plankton-like bacteria. Chlorine only kills bacteria suspended in the water along with the top of the slime layers of surfaces, but not all microorganisms since many microorganisms grow within the slime layer.

However, the disadvantages of chlorine are:
1. It has an unpleasant odor
2. It irritates the skin, and dries it
3. Many people are allergic to chlorine and their eyes become irritated if they come into contact with the chemical
4. Chlorine not only eliminates water-born bacteria but also destroys benevolent dermatological bacteria
5. Breathing directly above the water surface is irritating to the lungs
6. After a bath, people have to take a shower to eliminate chlorine residue
7. Chlorine is not environmentally friendly
8. People generally have to wash and/or treat their skin after a bath.

When water is treated with chlorine, it is necessary to keep the pH value between 7.2 and 7.8, because higher or lower pH values reduces chlorine efficiency. However there is no reason why water should not have a pH of around 8.2 like seawater of which the medical qualities are well-known.

In order to maintain the pH in chlorine treatment between the optimal values, it is necessary to dose pH+ or pH− additives. In practice, this means that the owner of a hot tub or pool is always measuring pH values to keep the water in good condition. Technically it is possible to control this by means of a computer, however the instruments are expensive. Besides chlorine, there are other methods for treating water, such as bromide. In combination with chlorine, it forms bromine. In most countries the use of bromide is forbidden due to suspected carcinogenic action by the formed bromate.

Up to now there is no solution for water treatment that will not irritate the skin or cause skin damage. Furthermore, there is an urgent need for water treatment additives that are environmentally friendly, healthy, gentle on the skin, that do not irritate the airways or the eyes.

BRIEF SUMMARY OF THE INVENTION

The present invention relates to compositions and their use for removing coatings from a substrate. The present invention is directed to a composition comprising (a) one or more metasilicate; (b) one or more carbonate; (c) one or more glyconate; and (d) one or more sulfate. The composition may also contain (d) salts, e.g., sea salts and other additives.

In another embodiment, the composition is suitable for removing a biofilm from a surface and which does not produce or comprise a peroxide, a terpene or sodium hypochlorite.

In another embodiment, the one or more metasilicate is an alkali metal silicate selected from the group consisting of sodium or potassium metasilicate, sodium or potassium orthosilicate and mixtures thereof.

In another embodiment, the one or more carbonate is selected from the group consisting of sodium carbonate, sodium sesquicarbonate, sodium sulfate,—sodium bicarbonate and mixtures thereof.

In another embodiment, the glyconate is selected from the group consisting of ammonium glyconate, lithium glyconate, sodium glyconate, sodium starch glyconate, potassium glyconate, ammonium acid glyconate, sodium acid glyconate, lithium acid glyconate, potassium acid glyconate, ammonium D-glyconate, lithium D-glyconate, sodium D-glyconate, potassium D-glyconate, glyconic acid, glyconic D acid, glyconic L acid, ammonium L-glyconate, lithium L-glyconate, sodium L-glyconate, potassium L-glyconate, magnesium glyconate, magnesium acid glyconate, magnesium D-glyconate, magnesium L-glyconate, calcium glyconate, calcium acid glyconate, calcium D-glyconate, calcium L-glyconate and mixtures thereof.

In another embodiment, the one or more sulfate is selected from the group consisting of potassium aluminum sulfate, sulfuric acid, sodium sulfate, potassium sulfate, lithium sulfate, ammonium sulfate, magnesium sulfate, strontium sulfate, aluminum sulfate, and mixtures thereof.

In one embodiment, the composition is free of chlorinated solvents, environmentally safe and user-friendly.

Another embodiment of the invention is a method for removing biofilm from, and/or for preventing biofilm from forming on, a surface, comprising adding an effective amount of a composition of the present invention to a water system.

In one embodiment, the method further comprising passing an ozone-containing gas through the water.

In one embodiment, the method further comprising irradiating the supply of water with ultraviolet radiation.

In one embodiment, the present methods and compositions are used in hot tubs or pools. In another embodiment, the hot tubs or pools have an ozonator and/or UV-C lamp to facilitate elimination of the microorganisms, e.g., planktonic bacteria, and a fine mesh filter is installed to capture the residues.

Without wishing to be bound by theory, it is believed that the methods and compositions of the present invention aid biofilm to detach from walls and pipes and to coagulate.

Biofilms are matrix-enclosed accumulations of microorganisms such as bacteria (with their associated bacteriophages), fungi, protozoa and viruses that may be associated with these elements. While biofilms are rarely composed of a single cell type, there are common circumstances where a particular cellular type predominates. The non-cellular components are diverse and may include carbohydrates, both simple and complex, proteins, including polypeptides, lipids and lipid complexes of sugars and proteins (lipopolysaccharides and lipoproteins).

Planktonic bacteria, which are metabolically active, are adsorbed onto a surface which has copious amounts of nutrients available for the initial colonization process. Once adsorbed onto a surface, the initial colonizing cells undergo phenotypic changes that alter many of their functional activities and metabolic paths. For example, at the time of adhesion, *Pseudomonas aeruginosa* (*P. aeruginosa*) shows upregulated algC, algD, algU etc. genes which control the production of phosphomanomutase and other pathway enzymes that are involved in alginate synthesis which is the exopolysaccharide that serves as the polysaccharide backbone for *P. aeruginosa*'s biofilm. As a consequence of this phenotypic transformation, as many as 30 percent of the intracellular proteins are different between planktonic and sessile cells of the same species.

Planktonic cells adsorb onto a surface, experience phenotypic transformations and form colonies. Once the colonizing cells become established, they secrete exopolysaccharides that serves as the backbone for the growing biofilm. While the core or backbone of the biofilm is derived from the cells themselves, other components e.g., lipids, proteins etc, over time, become part of the biofilm. Thus a biofilm is heterogeneous in its total composition, homogenous with respect to its backbone and heterogeneous with respect it its depth, creating diffusion gradients for materials and molecules that attempt to penetrate the biofilm structure.

Biofilm-associated or sessile cells predominate over their planktonic counterparts. Not only are sessile cells physiologically different from planktonic members of the same species, there is phenotypic variation within the sessile subsets or colonies. This variation is related to the distance a particular member is from the surface onto which the biofilm is attached. The more deeply a cell is embedded within a biofilm i.e., the closer a cell is to the solid surface to which the biofilm is attached or the more shielded or protected a cell is by the bulk of the biofilm matrix, the more metabolically inactive the cells are. The consequences of this variation and gradient create a true collection of communities where there is a distribution of labor, creating an efficient system with diverse functional traits, that is, build an eco system for the microorganisms.

Biofilm structures cause the reduced response of bacteria to chlorine and the bactericidal consequences of antimicrobial and sanitizing agents. Chlorine resistance and persistent infections that are refractory to treatments are a major problem in bacteriological transmissions, resistance to eradication and ultimately pathogenesis. While the consequences of bacterial resistance and bacterial recalcitrance are the same, there are two different mechanisms that explain the two processes.

In one embodiment, the microorganisms contained in the biofilm may subsequently be killed by ozone or UV-C equipment after putting into solution.

In another specific embodiment, the present methods and compositions are used in cooling water systems. In another specific embodiment, the present methods and compositions are used in water reservoir systems.

One skilled in the art will readily appreciate that the present invention is well adapted to carry out the objects and obtain the ends and advantages mentioned as well as those inherent therein. It should be understood, however, that the materials, compounds, coatings, methods, procedures, and techniques described herein are presently representative of preferred embodiments. These techniques are intended to be exemplary, are given by way of illustration only, and are not intended as limitations on the scope. Other objects, features, and advantages of the present invention will be readily apparent to one skilled in the art from the following detailed description; specific examples and claims; and various changes, substitutions, other uses and modifications that may be made to the invention disclosed herein without departing from the scope and spirit of the invention or as defined by the scope of the appended claims.

As used herein other than the claims, the terms "a," "an," "the," and "the" means one or more. As used herein in the claim(s), when used in conjunction with the words "comprises" or "comprising," the words "a," "an," "the," or "the" may mean one or more than one. As used herein "another" may mean at least a second or more.

As would be known to one of ordinary skill in the art, many variations of nomenclature are commonly used to refer to a specific chemical composition. Accordingly, several common alternative names may be provided herein in quotations and parentheses/brackets, or other grammatical technique, adjacent to a chemical composition's preferred designation when referred to herein. Additionally, many chemical compositions referred to herein are further identified by a Chemical Abstracts Service registration number. As would be known to those of ordinary skill in the art, the Chemical Abstracts Service provides a unique numeric designation, denoted herein as "CAS No.," for specific chemicals and some chemical mixtures, which unambiguously identifies a chemical composition's molecular structure.

In various embodiments described herein, exemplary values are specified as a range. It will be understood that herein the phrase "including all intermediate ranges and combinations thereof associated with a given range is all integers and sub-ranges comprised within a cited range. For example, citation of a range "0.03% to 0.07%, including all intermediate ranges and combinations thereof is specific values within the sited range, such as, for example, 0.03%, 0.04%, 0.05%, 0.06%, and 0.07%, as well as various combinations of such specific values, such as, for example, 0.03%, 0.06% and 0.07%, 0.04% and 0.06%, or 0.05% and 0.07%, as well as sub-ranges such as 0.03% to 0.05%, 0.04% to 0.07%, or 0.04% to 0.06%, etc.

Amounts of ingredients stated herein generally refer to the amount of the particular active ingredient (e.g., surfactant). Amounts stated for commercial products typically relate to the amount of the commercial product. The amount of active provided by the commercial product can be determined from the concentration of the commercial product and the fraction of the commercial product that is the active ingredient.

As used herein, the term "about" modifying the quantity of an ingredient in the compositions of the invention or employed in the methods of the invention refers to variation in the numerical quantity that can occur, for example, through typical measuring and liquid handling procedures used for making concentrates or use compositions in the real world; through inadvertent error in these procedures; through differences in the manufacture, source, or purity of the ingredients employed to make the compositions or carry out the methods; and the like. Whether or not modified by the term "about", it is intended that the claims include equivalents to the quantities.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All references, publications, patents, patent applications, and commercial materials mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

The above summary of the present invention is not intended to describe each embodiment or every implementation of the present invention. Advantages and attainments, together with a more complete understanding of the invention, will become apparent and appreciated by referring to the following detailed description and claims.

Further aspects and advantages of this invention will be disclosed in the following examples, which should be regarded as illustrative and not limiting the scope of this application.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

DETAILED DESCRIPTION OF THE INVENTION

Figure 1:
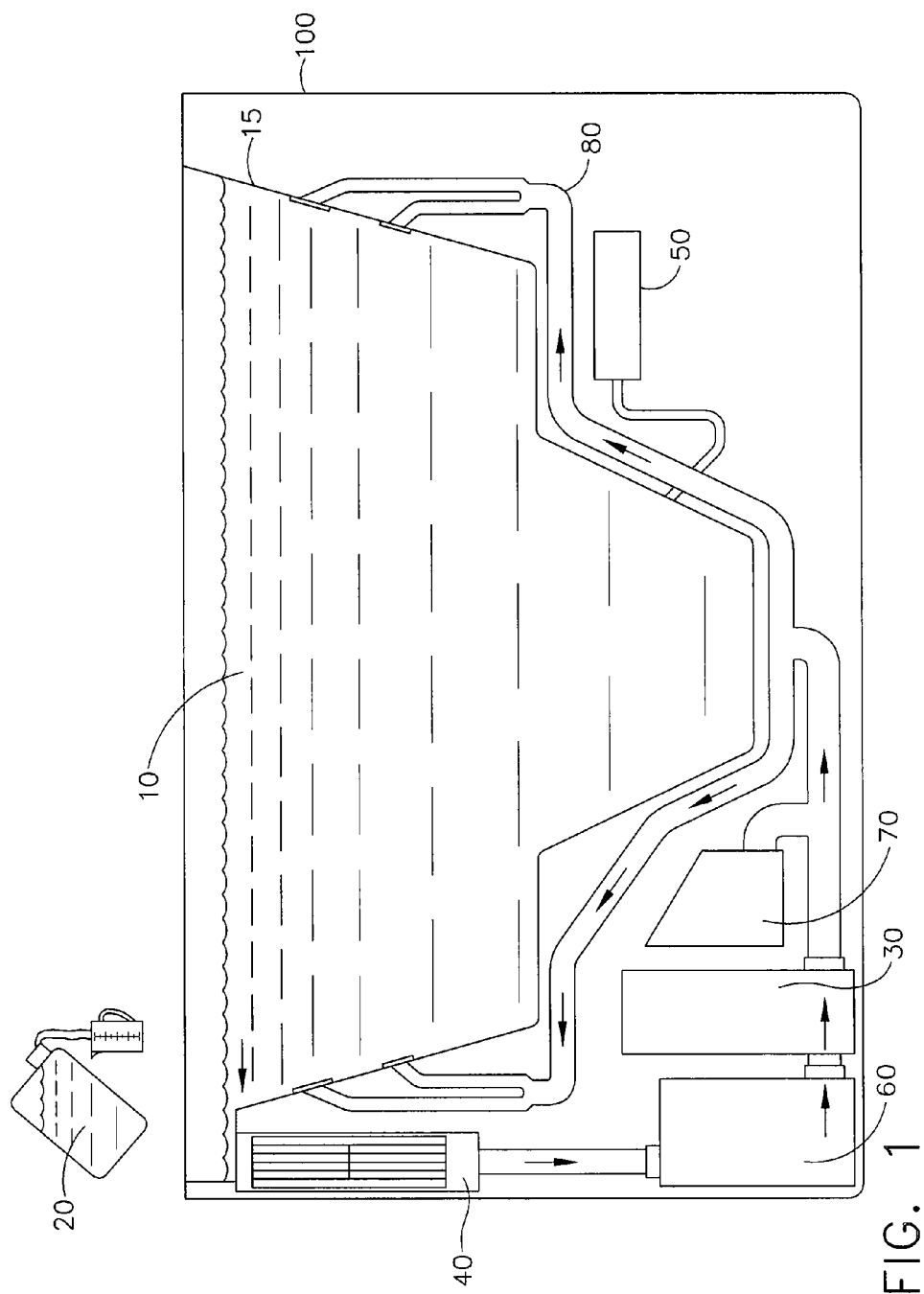
FIG. 1 provides a cross-sectional view of a hot tub.

The present invention relates to compositions and their use for the treatment of water. The present invention is directed to a composition comprising:

(a) one or more metasilicates
(b) one or more carbonate;
(c) one or more glyconate; and
(d) one or more sulfate or aluminum salt.

In one embodiment, the composition further comprises (e) an inorganic salt.

In one specific embodiment, the present invention provides for a composition comprising:
(a) one or more metasilicates
(b) one or more carbonate;
(c) one or more glyconate; and
(d) one or more sulfate or aluminum salt.

In another specific embodiment, the present invention provides for a composition additionally comprising:
(e) one or more inorganic salt.

In another specific embodiment, the present invention provides for a composition additionally comprising:
(f) one or more additional ingredients.

In one embodiment, the glyconate is selected from the group consisting of ammonium glyconate, lithium glyconate, sodium glyconate, sodium starch glyconate, potassium glyconate, ammonium acid glyconate, sodium acid glyconate, lithium acid glyconate, potassium acid glyconate, ammonium D-glyconate, lithium D-glyconate, sodium D-glyconate, potassium D-glyconate, glyconic acid, glyconic D acid, glyconic L acid, ammonium L-glyconate, lithium L-glyconate, sodium L-glyconate, potassium L-glyconate, magnesium glyconate, magnesium acid glyconate, magnesium D-glyconate, magnesium L-glyconate, calcium glyconate, calcium acid glyconate, calcium D-glyconate, calcium L-glyconate and mixtures thereof.

In one embodiment, the composition is in a dry or granulated state and can be combined with a suitable carrier, typically water, to form a solution. In another embodiment, the composition is in solution.

In one embodiment, the composition further comprises peroxygen compound. The peroxygen compound is preferably a perborate or a percarbonate and more preferably a percarbonate. The perborate or percarbonate preferably is complexed with a metal such as sodium, lithium, calcium, potassium or boron. The preferred percent by weight of the peroxygen compound in the composition, when in the dry or granular state, ranges from about 1% to about 40% and more preferably from about 2.5% to about 40%.

In another embodiment, the carbonate is a builder wherein the builder is at least one of the following compounds: a sodium carbonate (e.g., soda ash), sodium sesquicarbonate, sodium sulfate or sodium bicarbonate. In one embodiment, the carbonate is a hydrated carbonate such as trona. In one embodiment, the percent by weight of the builder in the cleaning composition, when in the dry or granular state, is from about 1% to about 75%. In another embodiment, the peroxygen compound, metasilicate and chelate are all salts having the same cation. In one embodiment, the cation is sodium or potassium.

A builder is also known as a sequestrant. A "sequestrant" is a molecule capable of coordinating (i.e., binding) the metal ions commonly found in natural water to prevent the metal ions from interfering with the action of the other ingredients of the composition. Some chelating/sequestering agents can also function as a threshold agent when included in an effective amount.

Optionally, the builders can be added, e.g., water soluble inorganic salt builders, preferably sodium salts, such as sodium polyphosphates, e.g. sodium tripolyphosphate and sodium pyrophosphate, sodium carbonate, sodium bicarbonate, sodium sesquicarbonate, sodium silicate, sodium disilicate, sodium metasilicate and sodium borate. In addition to the water soluble inorganic salts, water insoluble builders may also be useful, including the ion exchanging zeolites, such as Zeolite 4A. Organic builders may also be employed. Among suitable organic builders are polyacetal carboxylates, as described in U.S. Pat. No. 4,725,455, and water-soluble salts of lower hydroxycarboxylic acids, such as an alkali metal gluconate. Potassium or sodium gluconate are preferred.

Examples of aluminum salts suitable for use in the present invention include inorganic aluminum salts such as potassium aluminum sulfate, ammonium aluminum sulfate and aluminum chloride; and soluble aluminum carboxylates such as aluminum lactate, aluminum citrate and aluminum maleate.

Regarding these aluminum salts, in one embodiment, at least 90% by weight (hereinafter referred to as "%") or more of their particles have diameters of 200 micrometers or less. In one embodiment, at least 90% or more of the particles which make up the composition have diameters of 200 micrometers or less, and, in one embodiment, the average particle diameter falls within a range of 20-150. Ideally, the average particle diameter should be between 20 and 100 micrometers.

These aluminum salts can be used singly or in combination. It is preferred that the aluminum salts be incorporated into the composition in the range of 0.5-20%, preferably from 1-10% and more preferably from 1-5%, based on the total amount of the composition. Preferably, the concentration of aluminum salts within the bath water should fall within 0.5-80 ppm, more preferably 1-40 ppm. If the concentration is less than 0.5 ppm, a refreshing feeling is not imparted to the bather. If the concentration exceeds 80 ppm, insoluble substances precipitate out of the bath water.

In another embodiment, the carbonate used in the present invention is one or more carbonates selected from the group consisting of sodium carbonate, potassium carbonate, sodium bicarbonate, potassium bicarbonate, and sodium sesquicarbonate. In another embodiment, the carbonate used in the present invention is sodium carbonate and sodium bicarbonate. In another embodiment, the carbonates is incorporated in the composition in an amount of 10-98%, preferably 30-90%, based on the total amount of the composition.

In another embodiment, the carbonates in the water is 10 ppm or higher, preferably within the range of 10-400 ppm, and more preferably within 30-400 ppm.

Typical carbonates include sodium carbonate ($Na_2CO_3$), potassium carbonate ($K_2CO_3$) or other typical carbonate sources. Such carbonates can contain as an impurity some proportion of bicarbonate ($HCO_3^-$).

In another embodiment, the composition according to the present invention is prepared and used so that the pH of the final water falls between 7 and 9, and preferably within 7.0-8.5, when the composition is dissolved in the bath water. No limitation is imposed on the method of adjusting the pH of bath water. For example, the pH of bath water can be adjusted by changing the ratio of the above-mentioned components and the optional ingredients described hereinafter which are incorporated into the composition. The amounts of the above components are adjusted such that the pH of an aqueous 0.01% solution (4° C.) of the composition falls between 7 and 9.

In another embodiment, the composition, prior to final use, is prepared as a composition comprising:

| | |
|---|---|
| Meta Silicate | about 2-10 kg |
| Carbonate | about 2-10 kg |
| Glyconate | about 1-5 kg |
| Aluminum Sulfate | about 1-5 kg per 300 liters of water. |

In another embodiment, the composition, prior to final use, is prepared as a composition comprising:

| | |
|---|---|
| Meta Silicate | about 4-6 kg |
| Carbonate | about 4-5 kg |
| Glyconate | about 1-2 kg |
| Potassium Al Sulfate | about 1-2 kg per 300 liters of water. |

In another embodiment, the composition, prior to final use, is prepared as a composition comprising:

| | |
|---|---|
| MetaSilicate | about 2-10 kg |
| Carbonate | about 2-10 kg |
| Glyconate | about 1-5 kg |
| Potassium Al Sulfate | about 1-5 kg |
| Inorganic Salt | about 1-5 kg per 300 liters of water. |

In another embodiment, the composition, prior to final use, is prepared as a composition comprising:

| | |
|---|---|
| Meta Silicate | about 4-6 kg |
| Carbonate | about 4-5 kg |
| Glyconate | about 1-2 kg |
| Potassium Al Sulfate | about 1-2 kg |
| Inorganic Salt | about 1-2 kg per 300 liters of water. |

In another embodiment, the composition, prior to final use, is prepared as a composition comprising:

| | |
|---|---|
| Meta Silicate | about 4.9 kg |
| Sodium Carbonate | about 4.5 kg |
| Sodium Glyconate | about 1.5 kg |
| Potassium Al Sulfate | about 1.5 kg per 300 liters of water. |

In another embodiment, the composition, prior to final use, is prepared as a composition comprising:

| | |
|---|---|
| Meta Silicate | about 4.9 kg |
| Sodium Carbonate | about 4.5 kg |
| Sodium Glyconate | about 1.5 kg |
| Inorganic salt | about 1.5 kg |
| Potassium Al Sulfate | about 1.5 kg per 300 liters of water. |

In one specific embodiment, the present invention provides for a composition comprising:
(a) at least 1 mg/L of one or more metasilicates;
(b) at least 1 mg/L of one or more carbonate
(c) at least 0.5 mg/L of one or more glyconate; and
(d) at least 0.2 mg/L of one or more sulfate selected from the group consisting of potassium aluminum sulfate, sulfuric acid, sodium sulfate, potassium sulfate, lithium sulfate, ammonium sulfate, magnesium sulfate, strontium sulfate, and aluminum sulfate;
wherein the concentrations are the concentration in final solution in the water to be treated.

In another specific embodiment, the present invention provides for a composition additionally comprising:

(e) at least 0.6 mg/L of one or more salts.

In one specific embodiment, the present invention provides for a composition comprising:
(a) at least 1 mg/L of one or more metasilicates;
(b) at least 2 mg/L of one or more carbonate
(c) at least 0.8 mg/L of one or more glyconate; and
(d) at least 0.8 mg/L of one or more sulfate selected from the group consisting of potassium aluminum sulfate, sulfuric acid, sodium sulfate, potassium sulfate, lithium sulfate, ammonium sulfate, magnesium sulfate, strontium sulfate, and aluminum sulfate;
wherein the concentrations are the concentration in final solution in the water to be treated.

In another specific embodiment, the present invention provides for a composition additionally comprising:
(e) at least 1 mg/L of one or more salts.

In one specific embodiment, the present invention provides for a composition comprising:
(a) at least 3 mg/L of one or more alkali metal silicate selected from the group consisting of sodium or potassium metasilicate, orthosilicate or other water-soluble silicate;
(b) at least 3 mg/L of one or more carbonate selected from the group consisting of sodium carbonate, sodium sesquicarbonate, sodium sulfate and sodium bicarbonate;
(c) at least 0.9 mg/L of one or more glyconate; and
(d) at least 0.8 mg/L of one or more sulfate selected from the group consisting of potassium aluminum sulfate, sulfuric acid, sodium sulfate, potassium sulfate, lithium sulfate, ammonium sulfate, magnesium sulfate, strontium sulfate, and aluminum sulfate;
wherein the concentrations are the concentration in final solution in the water to be treated.

In another specific embodiment, the present invention provides for a composition additionally comprising:
(e) at least 0.6 mg/L of one or more salts.

In one specific embodiment, the present invention provides for a composition comprising:
(a) at least 1 mg/L of metasilicates;
(b) at least 2 mg/L of sodium carbonate
(c) at least 0.8 mg/L of sodium glyconate; and
(d) at least 0.8 mg/L of potassium aluminum sulfate;
wherein the concentrations are the concentration in final solution in the water to be treated.

In another specific embodiment, the present invention provides for a composition additionally comprising:
(e) at least 1 mg/L of one or more salts.

In one specific embodiment, the present invention provides for a composition comprising:
(a) from about 1 to about 100 mg/L of one or more metasilicates;
(b) from about 1 to about 100 mg/L of one or more
(c) from about 0.1 to about 60 mg/L of one or more glyconate; and
(d) from about 0.1 to about 100 mg/L of one or more sulfate,
wherein the concentrations are the concentration in final solution in the water to be treated.

In another specific embodiment, the present invention provides for a composition additionally comprising:
(e) from about 1 to about 100 mg/L of one or more salts.

In one specific embodiment, the present invention provides for a composition comprising:
(a) from about 1 to about 10 mg/L of one or more metasilicates;
(b) from about 1 to about 10 mg/L of one or more carbonate (c) from about 0.01 to about 6 mg/L of one or more glyconate; and
(d) from about 1 to about 10 mg/L of potassium aluminum sulfate,
wherein the concentrations are the concentration in final concentration in the water to be treated.

In another specific embodiment, the present invention provides for a composition additionally comprising:
(e) from about 1 to about 10 mg/L of one or more salts.

Additional Embodiments

| Substance | Range per liter water |
|---|---|
| Meta Silicate | 0.001-1,000 mg |
| Sodium Carbonate | 1.00-850 mg |
| Sodium Glyconate | 0.00-540 mg |
| Salt inorganic | 1.00-920 mg |
| Potassium Al Sulfate | 1.50-830 mg |
| Fragrances | |
| Another embodiment: | |
| Meta Silicate | 1.10-500 mg |
| Sodium Carbonate | 1.70-720 mg |
| Sodium Glyconate | 0.50-420 mg |
| Salt | 0.60-300 mg |
| Potassium Al Sulfate | 0.90-275 mg |
| Fragrances | |
| Another embodiment: | |
| Meta Silicate | 1.20-7.00 mg |
| Sodium Carbonate | 2.90-4.80 mg |
| Sodium Glyconate | 0.80-3.50 mg |
| Salt inorganic | 0.60-2.80 mg |
| Potassium Al Sulfate | 0.20-1.90 mg |
| Fragrances | |
| Another embodiment: | |
| Meta Silicate | 3.50-6.50 mg |
| Sodium Carbonate | 3.20-4.00 mg |
| Sodium Glyconate | 0.90-1.40 mg |
| Sea salt anorganic | 1.00-1.35 mg |
| Potassium Al Sulfate | 0.80-1.35 mg |
| Fragrances | 1.00-1.10 mg |

Against all expectations and documented evidence, the present inventors found that effective removal of biofilm may be achieved, using a solution comprising an amount of the composition described herein effective to treat a biofilm in a water system. In one embodiment, the water system is selected from the group consisting of hot tubs, spas, swimming pools, heat exchangers, cooling water systems, filtration systems, holding tanks, and small-scale reservoirs.

These compositions by themselves are sufficient to remove well-established biofilms in a period of time varying from within 1 hour to an indefinite time. In one embodiment, the treatment is between about 1 hour and 48 hours.

In accordance with the present invention, a method is provided for removing biofilm from, and/or for preventing biofilm from forming on, a surface of a vessel, conduit or other device that receives a supply of water. The method comprises adding to the supply of water a composition comprising: one or more metasilicate, one or more carbonate, one or more glyconate, and one or more sulfate.

In accordance with one embodiment of the present invention, a system is provided for removing biofilm from, and/or for preventing biofilm from forming on, a surface of a vessel, conduit or other device that receives a supply of water. In one embodiment, the system comprises a device a device for passing an ozone-containing gas through the water.

In accordance with another embodiment of the present invention, a system is provided for providing disinfected water to a conduit, and for removing biofilm from, and/or for preventing biofilm from forming on, an interior surface of a conduit. In another embodiment, system comprises an ultraviolet lamp disposed within an ultraviolet radiation permeable sleeve such that a channel is formed between an outer surface of the ultraviolet lamp and an inner surface of the sleeve. In another embodiment, an oxygen-containing gas is supplied to, and an ozone-containing gas is removed from, the channel. In another embodiment, the system includes a device for passing the ozone-containing gas to the conduit.

In accordance with yet another embodiment of the present invention, a system is provided for removing biofilm from, and/or for preventing biofilm from forming on, a surface of a vessel, conduit or other device that receives a supply of water. The system comprises a source of an ozone-containing gas, an ultraviolet irradiator for (a) receiving source water and producing disinfected water, or (b) receiving the ozone-containing gas and producing an ozone-diminished gas, a device for selectively routing either the disinfected water or the ozone-containing gas to the surface, and a device for selectively routing either the source water or the ozone-containing gas, downstream of the conduit, to the ultraviolet irradiator.

Ozone-containing gas removes biofilm much more efficiently than conventional disinfectants, such as chlorine. Also, because it is in a gaseous state, the ozone-containing gas is unlikely to leave a residual trace. Ozone digester further reduces the risk of harm from residual ozone. Generally, the ozone generator produces an ozone-containing gas, for example air+ozone, from an oxygen-containing gas, such as air. Alternatively, the oxygen-containing gas can be oxygen or oxygen-enriched air. The ozone-containing gas is produced by exposing oxygen-containing gas to a corona discharge or by irradiating oxygen-containing gas with ultra-violet radiation. The generation of ozone by shortwave ultraviolet radiation take place in the spectral region of 120 nm to 242 nm, with a peak output at 150 nm to 160 nm. The ultraviolet lamp is preferably a 185 nm wavelength lamp. A 185 nm wavelength lamp can produce approximately 0.5 grams per hour of ozone per 425 ma of lamp current, in dry air.

In one embodiment, the system includes an ultraviolet lamp is capable of producing radiation in a first wavelength range of about 120 nanometers to about 242 nanometers, preferably 185 nm, to induce the generation of a sufficient amount of ozone in the oxygen-containing gas. It is also capable of producing radiation in a second wavelength range of about 200 nanometers to about 300 nanometers, preferably 254 nm, in order to effectively kill most microorganisms such as airborne and surface bacteria, viruses, yeasts and molds. The ultraviolet lamp can be, for example, a dual wavelength low-pressure mercury lamp, or a medium pressure mercury lamp with a continuous spectrum. In one embodiment, the system includes an ozone digester. The ozone-containing gas is passed through ozone digester, which digests residual ozone.

In another embodiment of a system for removing biofilm from, and for preventing biofilm from forming on, a surface of a vessel, conduit or other device that receives a supply of water, and additionally for providing disinfected water to the surface. The system includes an ozone generator and a water disinfector.

In one embodiment, the system includes ozone generator, which supplies an ozone-containing gas. In one embodiment, the system includes a water disinfector, which supplies disinfected water.

In one embodiment, the system includes an ultraviolet lamp for irradiating untreated water from water source to produce disinfected water. The ultraviolet lamp generates ultraviolet radiation with a wavelength in the range of about 200 nanometers to about 300 nanometers. In another embodiment, the system includes ozone generator which includes an ultraviolet lamp for irradiating an oxygen-containing gas, such as pressurized air, to produce ozone-containing gas. The ultraviolet lamp generates ultraviolet radiation with a wavelength in the range of about 120 nanometers to about 242 nanometers.

Filters can be formed from at least one material selected from the group consisting of: activated carbon, activated carbon block, adsorption resins, ion exchange resins, zeolite, reduction catalysts, paper, polymers, clay, ceramics, metals, nylon, wood pulp, cellulose, cotton, fibers, and any other material capable of separating particulate, organics or inorganics from a feed stream. In one embodiment, the filter is in the form of one of the following: string wound filter, fiber composite molded filter, pleated filter, hollow fiber membrane, spiral wound membrane or sheet, plate and frame membrane and any other conventional form. When filter is used to remove organic materials, such as benzene, it is preferably formed of activated carbon or adsorption resin. To remove inorganic materials, such as heavy metals, or sulfites, the filter should be formed from ion exchange resin, zeolite or a reduction catalyst.

Another embodiment of a device suitable for use as a water disinfector is a PURA™ UV1-EPCB water purifier from Hydrotech, Inc. This product combines ultraviolet disinfection and carbon filtration in a compact system. In one embodiment, ultraviolet lamps, in consideration of its dual role, generates ultraviolet radiation with a first wavelength in the range of about 120 nanometers to about 242 nanometers, and a second wavelength in the range of about 200 nanometers to 300 nanometers.

Optionally, to prevent a release of any residual ozone from the system, the water can be directed to a filter (not shown) that destroys ozone by adsorption or reaction with wet granulated activated carbon, by contact with manganese dioxide, or by chemical reduction, such as by thiosulfate. In another embodiment, the system is controlled by a conventional computer or a programmable controller.

Optionally, the removal of biofilm from the system can be enhanced by periodically flushing it with a disinfectant, such as hypochlorite, chlorine dioxide ($ClO_2$) solution, hydrogen peroxide or other type of commercial disinfectant, such as BioVAC™ from Micrylium Labs. In one embodiment, the disinfectant flush is performed daily, weekly, monthly or every other month. The disinfectant solution may be introduced by means of a siphoned bottle (not shown) and a check valve (not shown), and the use of pressurized air as a driving force.

The ingredients may optionally be processed in an effective amount of an aqueous medium such as water to substantially blend and solubilize the ingredients and achieve a homogenous mixture, to aid in the hydration reaction if needed, to provide an effective level of viscosity for processing the mixture, and to provide the processed composition with the desired consistency. The water source is generally any source of water readily available. The water supply can also be bottled water, or water from any appropriate container or source, and the water can also be conditioned, such as by softening.

The highest concentrations confer a strength to the composition such as it is effective within one hour. The lowest concentrations confer a good performance within 18 hours.

Salts

In one embodiment, the composition utilizes a salt carrier. The salt carrier should not interfere with the compositions biological activity. When other materials are present, the salt carrier should not degrade those materials or interfere with their properties or biological activity. In other words, the salt carrier should be inert with respect to the other components.

In one embodiment, the composition can be formed into a tablet. A tablet according to the invention contains from about 40 to about 95 percent by weight of the salt carrier material. More preferably, the tablet contains about 50 to about 80 percent by weight of the matrix material, and most preferably from about 70 to about 80 percent.

The matrix material may be a single salt material or a mixture of two or more salts alone or in combination with other matrix materials. When the carrier matrix contains a mixture of salts, those salts are preferably present in equal amounts, e.g., a mixture of two salts in a 1:1 ratio. As discussed below, the ratio of salts may be adjusted to improve tablet stability, for example, by reducing the hygroscopicity of the carrier matrix.

The salt carrier is preferably a substantially water-soluble matrix. Preferably, the salt carrier is a water-soluble inorganic or organic salt or mixtures of such salts. For purposes of the present invention, water-soluble means having a solubility in water of about 0.2 grams per hundred grams of water at 20.degree. C.

Examples of suitable salts for the carrier matrix include various alkali metal and/or alkaline earth metal sulfates, chlorides, borates, bromides, citrates, acetates, lactates, etc. Specific examples of suitable salts include, but are not limited to, sodium acetate, sodium bicarbonate, sodium borate, sodium bromide, sodium carbonate, sodium chloride, sodium citrate, sodium fluoride, sodium gluconate, sodium sulfate, calcium chloride, calcium lactate, calcium sulfate, potassium sulfate, tripotassium phosphate, potassium chloride, potassium bromide, potassium fluoride, magnesium chloride, magnesium sulfate and lithium chloride. The preferred salts are the inorganic salts, especially the Group 1 or 2 metal sulfates and chlorides. Particularly preferred salts, because of their low cost, are sodium sulfate, and sodium chloride. Sodium chloride may be substantially pure or in the form of rock salt, sea salt, or dendrite salt.

As mentioned above, the salt carrier may contain other carrier materials, preferably in amounts from 0 to about 10 percent by weight of the tablet. These materials are preferably solid and include other carrier materials known in the art. These materials may be solid organic acids such as benzoic, gluconic, or sorbic acid. Use of such materials may allow the salt carrier to have beneficial activity, including biological activity, in the aqueous system. For example, gluconic acid, or its salts, may be used in a carrier matrix. But when the tablet is added to an aqueous system, the gluconic acid may additionally function as a metal chelant to sequester iron and prevent iron oxide staining.

Anti-Deposition Agent

The compositions of the present invention can also include an anti-redeposition agent capable of facilitating sustained suspension of coatings in a solution and preventing the removed coatings from being redeposited onto the substrate being cleaned. Examples of suitable anti-redeposition agents include surfactants, metasilicates, zeolites, fatty acid amides, fluorocarbon surfactants, complex phosphate esters, styrene maleic anhydride copolymers, and cellulosic derivatives such as hydroxyethyl cellulose, hydroxypropyl cellulose, and the like. The present composition can include about 0.5-15 wt. %, e.g., about 1-5 wt. %, of an anti-redeposition agent. Preferably, the re-deposition inhibitor is a surfactant, a metasilicate, a zeolite or any combination thereof.

In certain embodiments, the anti-redeposition agent is present at about 0.1 to about 30 wt. %, about 0.2 to about 10 wt. %, or about 0.5 to about 2 wt. %. In an embodiment, the anti-redeposition agent is present at about 1 wt. %. The composition can include any of these ranges or amounts not modified by about.

Alternatively, alkali metal silicate, alkali metal nitrite, alkali metal carbonate, and/or alkali metal phosphate components may be added to the composition of this invention. The alkali metal silicate component functions as both an alkalinity contributor as well as an anti re-deposition aid, is preferably present in the amount of between about 0.1 to 15 wt. % and is constituted by a sodium or potassium metasilicate, orthosilicate or other water-soluble silicate.

Additional Components

In addition to the above-noted components of the compositions of the invention, various optional adjuvants can be incorporated. These include thickeners, diluents, brighteners, fragrances, dyes, opacifiers, chelants, pH adjustants and anti-rust additives.

Corrosion inhibitors may optionally be added to the composition. Corrosion inhibitors, also known as anti-corrosive or anti-rust agents, reduce the degradation of the metallic parts contacted by the detergent and are incorporated at a level of about 0.1% to about 15%, and preferably about 0.5% to about 5% by weight of the total composition. The use of such corrosion inhibitors is preferred when the detergent is in contact with a metal surface. Suitable corrosion inhibitors include alkyl and aryl carboxylic acids and carboxylate salts thereof; sulfonates; alkyl and aryl esters; primary, secondary, tertiary and aryl amines; phosphoric esters; epoxides; mercaptans; and diols. Also suitable are the C12-C20 fatty acids, or their salts, especially aluminium tristearate; the C12-C20 hydroxy fatty acids, or their salts; and neutralized tall oil fatty acids. Phosphonated octa-decane and other anti-oxidants such as betahydroxytoluene (BHT) may also be used.

Other non-limiting examples of representative corrosion inhibitors include ethoxylated butynediol, petroleum sulfonates, blends of propargyl alcohol and thiourea. If used, the amount of such corrosion inhibitors is typically up to about 1, 2, 3, 4, 5, 6, 7, 8, 9 or 10% by weight of the total composition.

Other useful corrosion inhibitors include organic zinc complexes such as a zinc citrate, zinc hydroxy oxime complexes, and zinc copolymer complexes of acrylic acid ethacrylate; nitrogen and sulfur-containing aryl heterocycles; alkanolamines such as triethanolamine; amine-neutralized alkyl acid phosphates; dibasic acids-neutralized with amines, where the dibasic acids include, but are not limited to, adipic acid, succinic acid, sebacic acid, glutaric acid, malonic acid, suberic acid and examples of amines include, but are not limited to, methylamine, ethylamine, ethanolamine, diethanolamine, triethanolamine and N,N-dimethylcyclohexylamine, and mixtures thereof. Each of the above-mentioned anti-corrosives can be used individually or in combination thereof, or in combination with other types of additives.

Optionally, the compositions of the invention may also contain a thickener which functions not only as a viscosifying thickener but also as an emulsion stabilizing agent stabilizing the emulsions of the invention against separation at elevated temperatures. Illustrative thickeners which may be used in the practice of the invention include acrylic acid/alkyl methacrylate copolymers (Acrysol ICS-I or Acusol 820), carboxy acrylic polymers (Carbopol 940), guar gums, xanthan gums, polyacrylic acid crosslinked with polyalkenyl polyvinyl alcohol, ammonium alginate and sodium alginate. Other thickeners known to the art may also be used. When incorporated into the composition of the invention, preferably from approximately 0.1 to 2 wt. % of the thickener is used. The preferred thickeners include acrylic acid/alkyl methacrylate copolymers and carboxy acrylic polymers. Where the thickener component is one which contains free acidic groups (e.g. Accusol 820 or Carbopol 940), a neutralizing base such as mono-, di- or triethanolamine or other neutralizing base is incorporated to ionize or neutralize the free acid groups and produce the full thickening effect of the thickener component.

The use of one or more pH-adjusting agents, including minor amounts of mineral acids, basic compositions, and organic acids may be used. An exemplary composition includes citric acid, such as is available in an anhydrous salt form of an alkali metal citric acid. The addition of an effective amount of such a pH-adjusting agent is useful in establishing a targeted pH range for compositions according to the invention. The addition of an effective amount of a pH buffering composition so as to maintain the pH of the inventive compositions may also be added. While the composition of the invention generally does not require a pH buffering composition, the use of such a pH buffering composition may provide the benefit of hard water ion sequestration. Examples of such useful pH buffer compounds and/or pH buffering systems or compositions are alkali metal phosphates, polyphosphates, pyrophosphates, triphosphates, tetraphosphates, silicates, metasilicates, polysilicates, carbonates, hydroxides, and mixtures of the same. Certain salts, such as the alkaline earth phosphates, carbonates, hydroxides, can also function as buffers. It may also be suitable to use as buffers such materials as aluminosilicates (zeolites), borates, aluminates and certain organic materials such as gluconates, succinates, maleates, citrates, and their alkali metal salts. Such buffers keep the pH ranges of the compositions of the present invention within acceptable limits. Others, not particularly elucidated here may also be used. Preferably, citric acid, such as is available in an anhydrous salt form of an alkali metal citric acid is added as it is readily commercially available, and effective. The addition of such a buffering agent is desirable in certain cases wherein long term, i.e., prolonged storage, is to be anticipated for a composition, as well as insuring the safe handling of the aqueous composition.

In even more preferred embodiments, the composition further comprises biofilm dislodging enhancer agents such as chaotropic agents or calcium chelators.

A calcium chelator such as EDTA, preferably in a salt form, in a concentration of at least about 0.25% or any calcium chelator having a chelating potency substantially equivalent thereto may be added.

Chelators: Tetrasodium EDTA (0.25%-1%) has been tried with a certain degree of success against biofilms. Any chelator in a concentration equipotent to the above concentrations of EDTA is within the scope of this invention. It is worthwhile noting that HEEDTA has been used in the acid form (0.3%) and was good when another salt forming acid: acetic acid, was at a concentration of 0.1% to 1% and when the pH was brought from 2.42 to 5.0. So, chelator salts can be used or chelator acid precursors can be used in salt forming conditions. It is recalled that the chelator is an optional component; it is used to increase the cleaning strength of the solution. Its function is mainly to capture divalent ions such as $Ca^{2+}$ which are involved in EPS integrity.

A chaotropic agent such as SDS in a concentration of at least about 0.1% or any chaotropic agent having a chaotropic potency substantially equivalent thereto may also be added.

In more preferred embodiments, the compositions comprise at least about 0.1% SDS, at least about 0.1% acid, at least about 0.25% EDTA, the acid being selected from the group consisting of 2-ketoglutaric, acetic, iminodiacetic, mucic, glycolic, fumaric, aspartic, phosphoric, pyruvic, chloroacetic acids and alanine.

In a mostly preferred embodiment, the compositions comprise at least about 0.1% but less than 1% SDS, about 0.1%-2% acid, and at least about 0.25% but less than 1% EDTA, the acid being mandelic acid or any other of 2-ketoglutaric, acetic, iminodiacetic, mucic, glycolic, fumaric, aspartic, phosphoric, pyruvic, chloroacetic acids and alanine.

Chaotropic Agents: SDS has a dual action as a detergent and a chaotropic agent. Since a plurality of non-chaotropic detergents may substitute for SDS, the chaotropic activity is not considered essential to the claimed compositions. However, since SDS was the preferred detergent, it is contemplated that a chaotropic agent may be useful, as an optional component, in increasing the cleaning strength of the solution. Any chaotropic agent having the potency of in a concentration of at least about 0.1% SDS is within the scope of this invention.

Bactericides: When it is desirable to complete the cleaning solution with a bactericidal activity, especially in the medical field, a bactericide can be added in an effective concentration. It is recalled that bactericides alone are less effective against biofilms than against planktonic microorganisms. However, when bactericides are combined to a detergent/salt solution, or contacted with surfaces thereafter, they are capable of killing microorganisms which are retrieved as planktonic organisms and no longer organized as a biofilm, due to the detergent/acid/salt effect. Povidone-iodine 10%, mandelic acid 1%, sodium benzoate/salicylate 2%/0.2%, hydrogen peroxide 5%, sodium hypochlorite 0.5%, phenol 0.1% and CPC 0.1%-0.5% have all been tried with success, which indicates that any bactericide may be added in the cleaning solution in so far as the selected bactericide has a killing activity against the populations of microorganisms to eliminate.

Bactericidal Agents

Enzymatic enzymes include any member from the class of oxido-reductases, EC 1 that generate active oxygen; Monosaccharide oxidases, Peroxidases, Lactoperoxidases, Salivary peroxidases, Myeloperoxidases, Phenol oxidase, Cytochrome oxidase, Dioxygenases, Monooxygenases. The enzymes also include bacterial cell lytic enzymes, e.g., Lysozyme, Lactoferrin Other agents include antimicrobials e.g., chlorhexidine, amine fluoride compounds, fluoride ions, hypochlorite, quaterinary ammonium compounds e.g. cetylpyridinium chloride, hydrogen peroxide, monochloramine, providone iodine, any recognized sanitizing agent or oxidative agent and biocides.

Also included are antibiotics, including, but not limited to the following classes and members within a class:
Aminoglycosides: Gentamicin, Tobramycin, Netilmicin, Amikacin, Kanamycin, Streptomycin, Neomycin
Quinolones/Fluoroquinolones: Nalidixic Acid, Cinoxacin, Norfloxacin, Ciprofloxacin, Perfloxacin, Ofloxacin, Enoxacin, Fleroxacin, Levofloxacin
Antipseudomonal: Carbenicillin, Carbenicillin Indanyl, Ticarcillin, Azlocillin, Mezlocillin, Piperacillin
Cephalosporins: Cephalothin, Cephaprin, Cephalexin, Cephradine, Cefadroxil, Cefazolin, Cefamandole, Cefoxitin, Cefaclor, Cefuroxime, Cefotetan, Cefo-ranide, Cefuroxine Axetil, Cefonicid, Cefotaxime, Moxalactam, Ceftizoxime, Ceftriaxone, Cefoperazone, Cftazidime, Cephaloridine, Cefsulodin
Other beta-Lactam Antibiotics: Imipenem, Aztreonam beta-Lactamase Inhibitors: Clavulanic Acid, Augmentin, Sulbactam Sulfonamides: Sulfanilamide, Sulfamethoxazole, Sulfacetamide, Sulfadiazine, Sulfisoxazole, Sulfacytine, Sulfadoxine, Mafenide, p-Aminobenzoic Acid, Trimethoprim-Sulfamethoxazole Urinary Tract Antiseptics: Methenamine, Nitrofurantoin, Phenazopyridine and other napthpyridines Penicillins: Penicillin G and Penicillin V Penicillinase Resistant Methicillin, Nafcillin, Oxacillin, Cloxacillin, Dicloxacillin Penicillins for Gram-Negative/Amino Penicillins: Ampicillin (Polymycin), Amoxicillin, Cyclacillin, Bacampicillin Tetracyclines: Tetracycline, Chlortetracycline, Demeclocycline, Methacycline, Doxycycline, Minocycline Other Antibiotics Chloramphenicol (Chlormycetin), Erythromycin, Lincomycin, Clindamycin, Spectinomycin, Polymyxin B (Colistin), Vancomycin, Bacitracin Tuberculosis Drugs Isoniazid, Rifampin, Ethambutol, Pyrazinamide, Ethinoamide, Aminosalicylic Acid, Cycloserine Anti-Fungal Agents: Amphotericin B, Cyclosporine, Flucytosine Imidazoles and Triazoles: Ketoconazole, Miconazole, Itraconazole, Fluconazole, Griseofulvin Topical Anti Fungal Agents: Clotrimazole, Econazole, Miconazole, Terconazole, Butoconazole, Oxiconazole, Sulconazole, Ciclopirox Olamine, Haloprogin, Tolnaftate, Naftifine, Polyene, Amphotericin B, Natamycin The term "treat", "treating", or "treatment" as used herein refers to regulating a population of a deleterious microorganism that may form a biofilm. The population may be regulated by the compositions and methods of the present invention so that the microorganism is killed, thereby reducing the viable populations such as by bacteriocidal or fungicidal or the like. The methods and compositions of the present invention may maintain and not allow a population of a deleterious organism to increase or may prevent an invasion by a deleterious microorganism.

The term "pH buffering agent" as used herein refers to any organic or inorganic compound or combination of compounds that will maintain the pH of a solution to within about 0.5 pH units of a selected pH value. A "pH buffering agent" may be selected from, but is not limited to, Tris (hydroxymethyl) aminomethane (tromethaprim; TRIZMA base), or salts thereof, phosphates, amino acids, polypeptides or any other pH buffering agent or combination thereof.

As used herein, the term "antioxidant" is intended to mean an agent that inhibits oxidation and thus is used to prevent the deterioration of preparations by oxidation. Such compounds include, by way of example and without limitation, ascorbyl palmitate, butylated hydroxyanisole, butylated hydroxytoluene, monothioglycerol, sodium ascorbate, sodium formaldehyde sulfoxylate and sodium metabisulfite and others known to those of ordinary skill in the art. Other suitable antioxidants include, for example, BHT, BHA, sodium bisulfite, vitamin E and its derivatives, propyl gallate or a sulfite derivative.

Buffering agents are used to control the pH of an aqueous solution in which the film is immersed so as to maintain the pH of the core in the approximately neutral or alkaline range. A buffering agent is used to resist change in pH upon dilution or addition of acid or alkali. Such compounds include, by way of example and without limitation, potassium metaphosphate, potassium phosphate, monobasic sodium acetate and sodium citrate anhydrous and dihydrate, salts of inorganic or organic acids, salts of inorganic or organic bases, and others known to those of ordinary skill in the art.

Preservatives include compounds used to prevent the growth of microorganisms. Suitable preservatives include, by way of example and without limitation, benzalkonium chloride, benzethonium chloride, benzyl alcohol, cetylpyridinium chloride, chlorobutanol, phenol, phenylethyl alcohol, phenylmercuric nitrate and thimerosal and others known to those of ordinary skill in the art.

As used herein, the term "diluent" or "filler" is intended to mean inert substances used as fillers to create the desired bulk, flow properties, and compression characteristics in the preparation of the cores. Such compounds include, by way of example and without limitation, dibasic calcium phosphate, kaolin, lactose, sucrose, mannitol, microcrystalline cellulose, powdered cellulose, precipitated calcium carbonate, sorbitol, and starch and other materials known to one of ordinary skill in the art.

By the term "effective amount", it is understood that it is the amount or quantity of composition, which is sufficient to elicit the required or desired response, or in other words, the amount that is sufficient to elicit an appreciable biological response when administered to a water system.

Buffering agents help to maintain the pH in the range which approximates physiological conditions. They are preferably present at concentration ranging from about 2 mM to about 50 mM. Suitable buffering agents for use with the present invention include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, there may be mentioned phosphate buffers, histidine buffers and trimethylamine salts such as Tris.

Preservatives are added to retard microbial growth, and are added in amounts ranging from 0.2%-1% (w/v). Suitable preservatives for use with the present invention include phenol, benzyl alcohol, meta-cresol, methyl paraben, propyl paraben, octadecyldimethylbenzyl ammonium chloride, benzalconium halides (e.g., chloride, bromide, iodide), hexamethonium chloride, alkyl parabens such as methyl or propyl paraben, catechol, resorcinol, cyclohexanol, and 3-pentanol.

The formulation herein may also contain more than one active compound as necessary for the particular indication being treated, preferably those with complementary activities that do not adversely affect each other. The active ingredients may also be entrapped in microcapsule prepared, for example, by coascervation techniques or by interfacial polymerization, for example, hydroxymethylcellulose or gelatinmicrocapsule and poly-(methylmethacylate) microcapsule. Sustained-release preparations may be prepared. Suitable examples of sustained-release preparations include semi-permeable matrices of solid hydrophobic polymers, which matrices are in the form of shaped articles, e.g., films, or microcapsules.

For some uses, it might be desirable to add an anti-foamer. Also, a dye might be added to the compositions of this invention for easy monitoring of the extent of rinsing. In another embodiment, refreshing 30% of the water periodically will remove foam.

Various dyes, odorants including perfumes, and other aesthetic enhancing agents may also be included in the composition. Dyes may be included to alter the appearance of the composition, as for example, Direct Blue 86 (Miles), Fastusol Blue (Mobay Chemical Corp.), Acid Orange 7 (American Cyanamid), Basic Violet 10 (Sandoz), Acid Yellow 23 (GAF), Acid Yellow 17 (Sigma Chemical), Sap Green (Keyston Analine and Chemical), Metanil Yellow (Keystone Analine and Chemical), Acid Blue 9 (Hilton Davis), Sandolan Blue/Acid Blue 182 (Sandoz), Hisol Fast Red (Capitol Color and Chemical), Fluorescein (Capitol Color and Chemical), Acid Green 25 (Ciba-Geigy), and the like. Fragrances or perfumes that may be included in the compositions include, for example, terpenoids such as citronellol, aldehydes such as amyl cinnamaldehyde, a jasmine such as CIS-jasmine or jasmal, vanillin, and the like.

In another embodiment, bleaching agents for use in the compositions for lightening or whitening a substrate can be included, include bleaching compounds capable of liberating an active halogen species, such as Cl2, Br2, -OCl.sup.- and/or -OBr.sup.-, under conditions typically encountered during the cleansing process. Suitable bleaching agents for use in the present compositions include, for example, chlorine-containing compounds such as a chlorine, a hypochlorite, chloramine. Preferred halogen-releasing compounds include the alkali metal dichloroisocyanurates, chlorinated trisodium phosphate, the alkali metal hypochlorites, monochloramine and dichloramine, and the like. Encapsulated chlorine sources may also be used to enhance the stability of the chlorine source in the composition (see, for example, U.S. Pat. Nos. 4,618,914, and 4,830,773, the disclosure of which is incorporated by reference herein). A bleaching agent may also be a peroxygen or active oxygen source such as hydrogen peroxide, perborates, sodium carbonate peroxyhydrate, phosphate peroxyhydrates, potassium permonosulfate, and sodium perborate mono and tetrahydrate, with and without activators such as tetraacetylethylene diamine, and the like. A composition may include a minor but effective amount of a bleaching agent, preferably about 0.1-10 wt-%, preferably about 1-6 wt-%.

In one embodiment, the compositions of the present invention are used in combination with an ozonator and/or UV-C lamp. In another embodiment, the compositions of the present invention force biofilms to release from walls and pipes and coagulates the resulting residues.

In another embodiment, the compositions of the present invention are used in methods of treating water. Begin with a clean hot tub or pool filled with clear, fresh water, or clear water previously treated with chlorine. Pour out the appropriate dosage of the product on the water surface. Jets in the hot tub, or pumps in the swimming pool, should be activated to ensure that the product mixes with the water.

In one embodiment, the composition is added to the water to be treated on a continuous manner. In another embodiment, it is added daily. In another embodiment, it is added weekly.

In another embodiment, water includes a filter. In another embodiment, the filter is cleaned once or twice per week with the filter cleaner delivered with the compositions of the present invention.

In another embodiment, the compositions are used in a pool. In another embodiment, the pool filter is backwashed. In another embodiment, the pool filter is backwashed once or twice a week. In another embodiment, the filter is a zeolite filter. Zeolite filter is preferred In another embodiment, the pool filter is a sand filter.

| CONTENTS IN LITRES OF HOTTUB | ADD WEEKLY IN MILILITER | CONTENTS IN LITRES OF POOL | ADD WEEKLY IN LITRES |
| --- | --- | --- | --- |
| 800-900 | 225 | 2,500 | 0.1 |
| 900-1,000 | 250 | 5,000 | 0.2 |
| 1,000-1,100 | 275 | 10,000 | 0.4 |
| 1,100-1,200 | 300 | 20,000 | 0.5 |
| 1,200-1,300 | 325 | 30,000 | 1.2 |
| 1,300-1,400 | 350 | 40,000 | 1.6 |
| 1,400-1,500 | 375 | 50,000 | 2.0 |
| 1,500-1,600 | 400 | 60,000 | 2.4 |
| 1,600-1,700 | 425 | 70,000 | 2.8 |
| 1,700-1,800 | 450 | 80,000 | 3.2 |
| 1,800-1,900 | 475 | 90,000 | 3.6 |
| 1,900-2,000 | 500 | 100,000 | 4.0 |

The solution concentrates of the invention further include water sufficient to provide the remaining weight of the composition. Deionized or distilled water is preferably employed.

The present water additive composition may contain the following optional ingredients if desired:

(a) inorganic acids such as boric acid, metasilicic acid and silicic anhydride;

(b) inorganic salts such as sodium chloride, sodium sulfate, potassium nitrate, sodium nitrate, calcium nitrate, sodium polyphosphate, ammonium chloride, ferrous sulfate, sodium phosphate and sodium thiosulfate;

(c) crude drugs such as atractylodes rhizoma, atractylodes macrocephala, Japanese valerian, nepeta japonica, magnolia bark, cnidium rhizoma, bitter orange peel, ligusticum, powdered ginger, ginseng, cinnamon, paeoniae radix, peppermint leaves, Scutellariae radix, gardenias fructus, tackahoe, angelicae tuhou radix, calamus root, artemisias argyi folium, schisandra repanda, angelica dahurica root, houttuynia cordata, bomeol, suffron crocus, phellodendron extract, citrus unshiu peel, fennel, citri pericarpium pulveratum, camomile, melissa, rosemary, horse chestnut, milfoil and mountain amica.

(d) oils and fats such as isopropylpalmitate, isopropylmyristate, cholesteryl isostearate, squalane, tri(capryl-capric acid) glycerol, rice-bran oil, rice-bran extract, 1-isostearoyl-3-myristoyl-glycerol, olive oil, jojoba oil, soybean oil, liquid paraffin and white Vaseline;

(e) alcohols such as ethanol, stearyl alcohol, isopropyl alcohol, cetyl alcohol and hexadecyl alcohol;

(f) polyols such as glycerol, propylene glycol and sorbitol;

(g) surfactants such as alkyl sulfate, polyoxyethylene alkyl ether sulfate, lauric acid diethanolamide, polyoxyethylene alkyl ether, polyethylene glycol monostearate; and (h) other ingredients such as titanium oxide, zinc oxide, talc, sulfur, ore sand, neutral terra abla, sodium salicylate, yolk powder, parched rice-bran, mica powder and powdered skim milk.

The water additive compositions of this invention may further include preservatives, moisturizers, metal sequestering and chelating agents, perfumes and other ingredients. The compositions of the present invention are prepared by conventional methods to form powders, granules, tablets and the like.

The preferred embodiments are exemplified by the following nonlimiting examples.

EXAMPLES

Example 1

FIG. 1. is a cross-sectional view of a hot tub (100) to be treated. Circulation of water (10) is illustrated, which begins in the hot tub water reservoir (15) itself where the surface water (10) flows through the filter (40). After the water (10) has been filtered, the water (10) passes through the heater (60) and from the heater (60) through the pump (30). After that, the water (10) flows back into the hot tub water reservoir (15). The flow can be controlled by the power of the pump (30) and there is a possibility to inject extra air into the water though the air control unit (70). An ozonator (50) is installed separately, and injects $O_3$ into the water (10) to kill the bacteria. The bubbles from the ozonator (50) enter the water (10) through the "ozonator exit" opening. The ozonator (50) is controlled according to the pollution level: from three times two hours in a twenty-four hour period, to six times two hours in a twenty-four period. In one instance, the ozonator (50) runs six times for two hours each, in a twenty-four hour period.

Example 2

Figure 2:
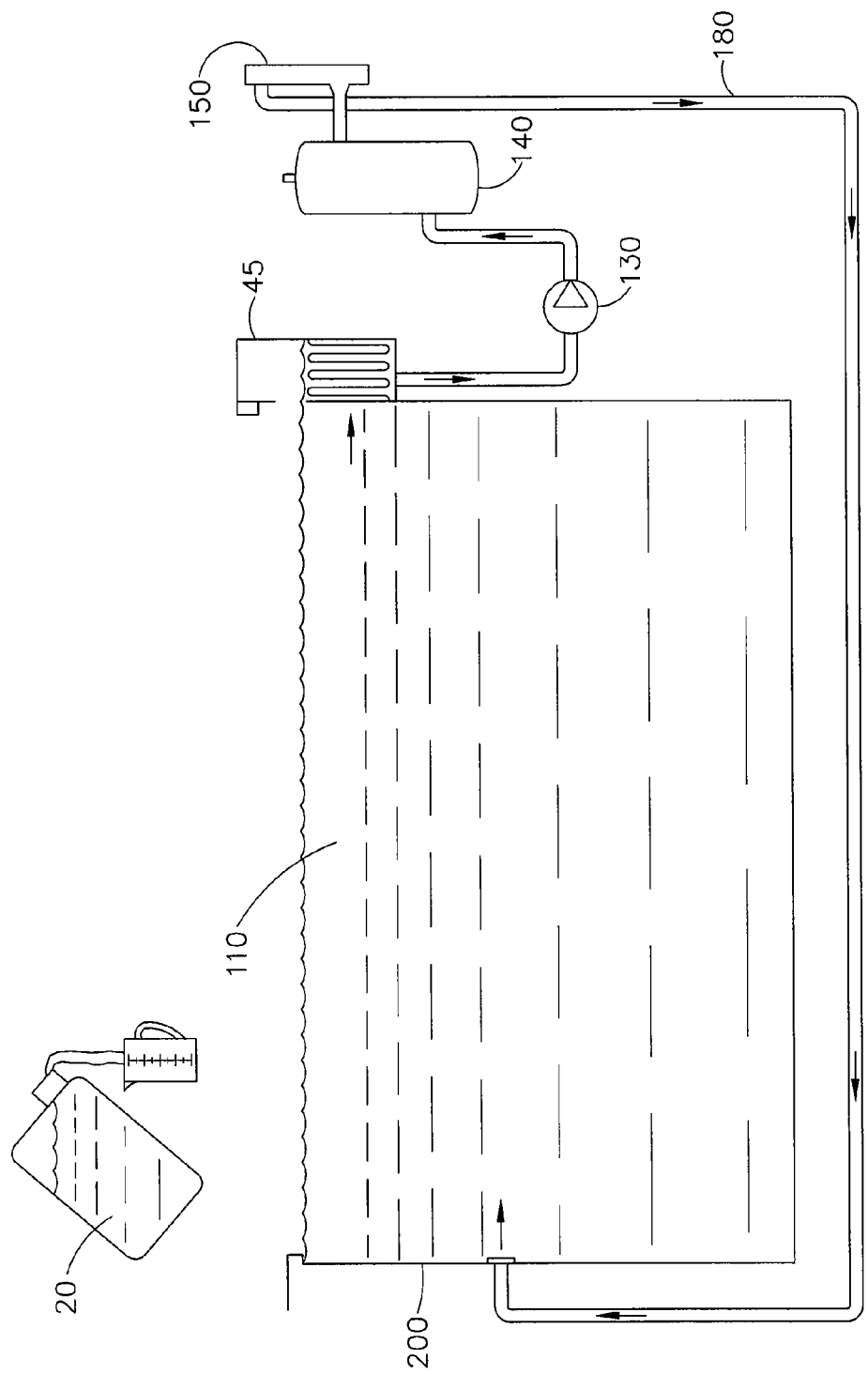
FIG. 2 depicts a cross-sectional view of a pool.

FIG. 2. is a cross-sectional view of a pool (200) to be treated. The water treatment composition (20) of the present invention is poured onto the water surface. Circulation of water (110) is illustrated, which begins in the pool (200) itself where the surface water (110) enters into the skimmer (45). From the skimmer (45) the water (110) goes through the filter (140) and from there the water (110) passes near the UV-C lamp and/or ozonator (150) for disinfection. After this the water (110) returns to the pool (200) through jets. Generally, at least once a week the filter (140) is backwashed. The wastewater flows into the sewer system. In this system, the wastewater is not polluted with chemicals that can damage the environment.

The description fully satisfies the objects, aspects and advantages set forth. While the invention has been set forth in conjunction with specific embodiments thereof, it is evident that many alternatives, modifications, and variations will be apparent to those skilled in the art in the light of the foregoing description. Accordingly, it is intended to embrace all such alternatives, modifications, and variations which fall within the spirit and scope of the following claims.

I claim:

1. A composition for controlling the growth of microorganisms comprising an aqueous solution of:
    (a) about 13-20 g/L metasilicate;
    (b) about 13-17 g/L carbonate;
    (c) about 3-7 g/L glyconate; and
    (d) about 3-7 g/L potassium aluminum sulfate.
2. The composition of claim 1, wherein the one or more metasilicate is an alkali metal silicate selected from the group consisting of sodium or potassium metasilicate, and mixtures thereof.
3. The composition of claim 1, wherein the one or more carbonate is selected from the group consisting of sodium carbonate, sodium sesquicarbonate, sodium bicarbonate and mixtures and hydrated carbonates thereof.

4. The composition of claim 1, wherein the one or more glyconate is selected from the group consisting of ammonium glyconate, lithium glyconate, sodium glyconate, sodium starch glyconate, potassium glyconate, ammonium D-glyconate, lithium D-glyconate, sodium D-glyconate, potassium D-glyconate, glyconic acid, glyconic D acid, glyconic L acid, ammonium L-glyconate, lithium L-glyconate, sodium L-glyconate, potassium L-glyconate, magnesium glyconate, magnesium acid glyconate, magnesium D-glyconate, magnesium L-glyconate, calcium glyconate, calcium acid glyconate, calcium D-glyconate, calcium L-glyconate and mixtures thereof.

5. The composition of claim 1, wherein the pH of an aqueous 0.01% solution of the composition at 40° C. falls between 7 and 9.

6. The composition of claim 1, wherein the composition does not produce or comprise a peroxide, a terpene or sodium hypochlorite.

7. The composition as defined in claim 1, which further comprises a biofilm dislodging enhancer agent selected from the group consisting of a chaotropic agent or a calcium chelator.

8. The composition as defined in claim 4, wherein the composition is prepared as an aqueous solution comprising from about 2 mM to about 50 mM of one or more buffering agents.

9. A method for removing biofilm from, and/or for preventing biofilm from forming on a surface on a water system, comprising adding an effective amount of a composition of any one of claims 1, 2-6, 7, and 8, to the water system.

10. The method of claim 9, further comprising passing an ozone-containing gas through the water system.

11. The method of claim 9, further comprising irradiating water that is used to supply the water system with ultraviolet radiation.

12. The method of claim 11, wherein the ultraviolet radiation includes a wavelength in the range of about 100 nanometers to about 300 nanometers.

13. The method of claim 11, wherein the pH of the water system after addition of the composition falls between 7 and 9.

14. The method of claim 10, further comprising generating the ozone-containing gas from an oxygen-containing gas, wherein the oxygen-containing gas is at least one selected from the group consisting of: air, oxygen and oxygen-enriched air.

15. The composition as defined in claim 8, wherein the composition, further comprises about 0.2 to about 10 wt. %, of an anti-redeposition agent.

16. The composition of claim 15, wherein the composition further comprises about 0.1% to about 15% anti-corrosive agent.

17. A method for treating medical waste or equipment, comprising adding an effective amount of a composition of any one of claims 1, 2-6, 7, and 8 to a water system.

18. A method for regulating a population of deleterious microorganisms comprising treating the microorganisms with the composition of claim 8.

19. The composition of claim 1, wherein the metasilicate is sodium metasilicate, the carbonate is sodium carbonate, and the glyconate is sodium glyconate.

20. The composition as defined in claim 1, wherein the composition, prior to final use, is prepared as an aqueous solution, the composition comprising:

| (a) Meta Silicate | about 4-6 kg; |
| --- | --- |
| (b) Carbonate | about 4-5 kg; |
| (c) Glyconate | about 1-2 kg; and |
| (d) Potassium Aluminum Sulfate | about 1-2 kg; per 300 liters of water. |

21. The composition as defined in claim 1, wherein the composition, prior to final use, is prepared as an aqueous solution, the composition comprising:

| (a) Meta Silicate | about 16 g/L; |
| --- | --- |
| (b) Sodium Carbonate | about 15 g/L; |
| (c) Sodium Glyconate | about 5 g/L; and |
| (d) Potassium Al Sulfate | about 5 g/L. |

22. A composition, wherein the composition is an aqueous solution comprising:
(a) at least 1 mg/L of one or more meta silicates;
(b) at least 1 mg/L of one or more carbonate;
(c) at least 0.5 mg/L of one or more glyconate; and
(d) at least 0.2 mg/L of one or more sulfate selected from the group consisting of potassium aluminum sulfate, sulfuric acid, sodium sulfate, potassium sulfate, lithium sulfate, ammonium sulfate, magnesium sulfate, strontium sulfate, and aluminum sulfate; wherein at least one of sulfate is potassium aluminum sulfate;
wherein the concentrations are the concentration in final solution in the water to be treated.

23. The composition of claim 22, wherein the composition further comprises
(e) at least 0.6 mg/L of one or more salts.

24. The composition of claim 22, wherein the composition is an aqueous solution comprising:
(a) at least 1 mg/L of one or more meta silicates;
(b) at least 2 mg/L of one or more carbonate
(c) at least 0.8 mg/L of one or more glyconate; and
(d) at least 0.8 mg/L of one or more sulfate selected from the group consisting of potassium aluminum sulfate, sulfuric acid, sodium sulfate, potassium sulfate, lithium sulfate, ammonium sulfate, magnesium sulfate, strontium sulfate, and aluminum sulfate; wherein at least one of sulfate is potassium aluminum sulfate;
wherein the concentrations are the concentration in final solution in the water to be treated.

25. The composition of claim 24, wherein the composition further comprises
(e) at least 1 mg/L of one or more salts.

26. The composition of claim 22, wherein the composition is an aqueous solution comprising:
(a) at least 3 mg/L of one or more alkali metal silicate selected from the group consisting of sodium or potassium metasilicate, orthosilicate or other water-soluble silicate;
(b) at least 3 mg/L of one or more carbonate selected from the group consisting of sodium carbonate, sodium sesquicarbonate, and sodium bicarbonate;
(c) at least 0.9 mg/L of one or more glyconate; and
(d) at least 0.8 mg/L of one or more sulfate selected from the group consisting of potassium aluminum sulfate, sulfuric acid, sodium sulfate, potassium sulfate, lithium sulfate, ammonium sulfate, magnesium sulfate, strontium sulfate, and aluminum sulfate; wherein at least one of sulfate is potassium aluminum sulfate;
wherein the concentrations are the concentration in final solution in the water to be treated.

27. The composition of claim 26, wherein the composition further comprises
(e) at least 0.6 mg/L of one or more salts.

28. The composition of claim 22, wherein the composition is an aqueous solution comprising:
(a) at least 1 mg/L of meta silicates;
(b) at least 2 mg/L of sodium carbonate
(c) at least 0.8 mg/L of sodium glyconate; and
(d) at least 0.8 mg/L of potassium aluminum sulfate;
wherein the concentrations are the concentration in final solution in the water to be treated.

29. The composition of claim 28, wherein the composition further comprises
(e) at least 1 mg/L of one or more salts.

30. The composition of claim 22, wherein the composition is an aqueous solution comprising:
(a) from about 1 to about 100 mg/L of one or more alkali metal silicate selected from the group consisting of sodium or potassium metasilicate, and mixtures thereof;
(b) from about 1 to about 100 mg/L of one or more carbonate selected from the group consisting of sodium carbonate, sodium sesquicarbonate and sodium bicarbonate
(c) from about 0.1 to about 60 mg/L of sodium glyconate; and
(d) from about 0.1 to about 100 mg/L of potassium aluminum sulfate,
wherein the concentrations are the concentration in final solution in the water to be treated.

31. The composition of claim 30, wherein the composition further comprises
(e) from about 1 to about 100 mg/L of one or more salts.

32. The composition of claim 22, wherein the composition is an aqueous solution comprising:
(a) from about 1 to about 10 mg/L of one or more meta silicates;
(b) from about 1 to about 10 mg/L of one or more carbonate
(c) from about 0.5 to about 6 mg/L of one or more glyconate;
(d) from about 1 to about 10 mg/L of potassium aluminum sulfate, and
(e) from about 1 to about 10 mg/L of one or more salts,
wherein the concentrations are the concentration in final concentration in the water to be treated.

33. A composition, wherein the composition is an aqueous solution comprising:

| (a) Meta Silicate | 1.20-7.00 mg/L; |
| --- | --- |
| (b) Sodium Carbonate | 2.90-4.80 mg/L; |
| (c) Sodium Glyconate | 0.80-3.50 mg/L; |
| (d) Salt inorganic | 0.60-2.80 mg/L; and |
| (e) Potassium Al Sulfate | 0.20-1.90 mg/L. |

34. The composition of claim 33, wherein the composition is an aqueous solution comprising:

| (a) Meta Silicate | 3.50-6.50 mg/L; |
| --- | --- |
| (b) Sodium Carbonate | 3.20-4.00 mg/L; |
| (c) Sodium Glyconate | 0.90-1.40 mg/L; |
| (d) Sea salt | 1.00-1.35 mg/L; |
| (e) Potassium Al Sulfate | 0.80-1.35 mg/L; and |
| (f) Fragrances | 1.00-1.10 mg/L. |

35. The composition of claim 33, wherein the composition has a pH of from 7 to 8.5.

* * * * *